United States Patent [19]

Krämer et al.

[11] Patent Number: 4,935,049
[45] Date of Patent: Jun. 19, 1990

[54] SUBSTITUTED AZOLYLMETHYLCARBINOLS

[75] Inventors: Wolfgang Krämer, Burscheid; Erik Regel, Wuppertal; Karl H. Büchel, Burscheid; Stefan Dutzmann, Duesseldorf; Wilhelm Brandes, Leichlingen; Klaus Lürssen, Bergisch-Gladbach, all of Fed. Rep. of Germany

[73] Assignee: Bayer Aktiengesellschaft, Leverkusen, Fed. Rep. of Germany

[21] Appl. No.: 255,207

[22] Filed: Oct. 7, 1988

[30] Foreign Application Priority Data

Oct. 14, 1987 [DE] Fed. Rep. of Germany ....... 3734694
Sep. 6, 1988 [DE] Fed. Rep. of Germany ....... 3830240

[51] Int. Cl.$^5$ .................... C07D 417/06; A01N 43/78
[52] U.S. Cl. ........................................ 71/90; 540/603; 544/60; 544/367; 544/133; 546/276; 546/278; 548/193; 548/205
[58] Field of Search ..................... 548/205, 193; 71/90; 540/603; 544/60, 133, 367; 546/276, 278

[56] References Cited

FOREIGN PATENT DOCUMENTS 0158205 10/1985 European Pat. Off. ............... 71/90

Primary Examiner—Robert Gerstl
Attorney, Agent, or Firm—Sprung Horn Kramer & Woods

[57] ABSTRACT

New substituted azolylmethylcarbinols of the formula

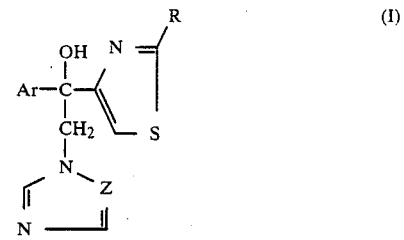

in which
Ar stands for optionally substituted aryl,
Z stands for nitrogen or an CH group and
R stands for alkyl, dialkylaminoalkyl, alkenyl, alkinyl, alkoxyalkyl, optionally substituted aralkyl, optionally substituted aryloxyalkyl, optionally substituted aryl or a radical of the formula

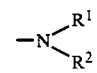

wherein
$R^1$ stands for hydrogen, alkyl, alkenyl, alkinyl or cycloalkyl and
$R^2$ stands for hydrogen, alkyl, alkoxyalkyl, alkenyl, alkinyl, cycloalkyl, cycloalkylalkyl, for optionally substituted aryl or for optionally substituted aralkyl, or
$R^1$ and $R^2$ together with the nitrogen atom to which they are bonded stand for an optionally substituted heterocyclic ring which cna optionally contain further heteroatoms, and acid addition salts and metal salt complexes thereof, and the use of the novel compounds as fungicides and plant growth regulators.

14 Claims, No Drawings

SUBSTITUTED AZOLYLMETHYLCARBINOLS

The present invention relates to new substituted azolylmethylcarbinols, to fungicidal and plant growth regulating compositions containing them, and to their use as fungicides and plant growth regulators.

It is known that certain substituted azolylmethylcarbinols have good fungicidal properties (cf. DE-OS (German Published Specification) 3,413,173). Thus, for example, 1-(4-chlorophenyl)-1-(4,5-dimethyl-thiazol-2-yl)-2-(1,2,4-triazol-1-yl)-ethanol and 1-(2,4-dichlorophenyl)-1-(4,5-dimethyl-thiazol-2-yl)-2-(1,2,4-triazol-1-yl)-ethanol can be used for combating fungi. However, the activity of these compounds is not completely satisfactory in all fields of application, especially at low application rates and concentrations. In addition, nothing is known concerning a plant growth-regulating activity of these previously known substances.

The present invention now provides, as new compounds, the substituted azolylmethylcarbinols of the formula

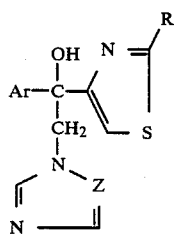

(I)

in which
Ar stands for optionally substituted aryl,
Z stands for nitrogen or a CH group and
R stands for alkyl, dialkylaminoalkyl, alkenyl, alkinyl, alkoxyalkyl, optionally substituted aralkyl, optionally substituted aryloxyalkyl, optionally substituted aryl or a radical of the formula

wherein
R¹ stands for hydrogen, alkyl, alkenyl, alkinyl or cycloalkyl and
R² stands for hydrogen, alkyl, alkoxyalkyl, alkenyl, alkinyl, cycloalkyl, cycloalkylalkyl, for optionally substituted aryl or for optionally substituted aralkyl, or
R¹ and R² together with the nitrogen atom to which they are bonded stand for an optionally substituted heterocyclic ring which can optionally contain further heteroatoms,
and acid addition salts and metal salt complexes theeof.

The substituted azolylmethylcarbinols of the formula (I) contain an asymmetrically substituted carbon atom and can therefore be obtained in the two optically isomeric forms or also as isomer mixtures of varying composition. The invention relates both to the racemates and to the individual isomers and their mixtures.

Furthermore, it has been found that the new substituted azolylmethylcarbinols of the formula (I) and their acid addition salts and metal salt complexes are obtained when substituted 2-bromoethanols of the formula

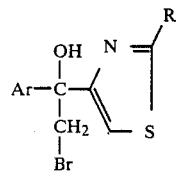

(II)

in which
Ar and R have the given meaning, are reacted with azoles of the formula

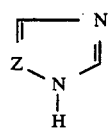

(III)

in which
Z has the abovementioned meaning,
if appropriate in the presence of a diluent and if appropriate in the presence of a reaction auxiliary and also if appropriate in the presence of a phase transfer catalyst, and the reaction product is then subjected, if appropriate, to an addition reaction with an acid or a metal salt.

Finally, it has been found that the new substituted azolylmethylcarbinols of the formula (I) and their acid addition salts and metal salt complexes have very good fungicidal and plant growth-regulating properties.

Surprisingly, the active compounds according to the invention show a considerably better fungicidal activity than 1-(4-chlorophenyl)-1-(4,5-dimethyl-thiazol-2-yl)-2-(1,2,4-triazol-1-yl)-ethanol and 1-(2,4-dichlorophenyl)-1-(4,5-dimethyl-thiazol-2-yl)-2-(1,2,4-triazol-1-yl)-ethanol, which are constitutionally similar, previously known active compounds of the same type of action.

Formula (I) provides a general definition of the substituted azolylmethylcarbinols according to the invention. Preferred compounds of the formula (I) are those in which
Ar stands for phenyl which can be monosubstituted or polysubstituted by identical or different substituents from the series comprising halogen, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different halogen atoms, such as fluorine, chlorine or bromine atoms, by straight-chain or branched halogenoalkoxy having 1 to 4 carbon atoms and 1 to 9 identical or different halogen atoms, such as fluorine, chlorine or bromine atoms, and/or by straight-chain or branched halogenoalkylthio having 1 to 4 carbon atoms and 1 to 9 identical or different halogen atoms, such as fluorine, chlorine or bromine atoms, Z stands for nitrogen or a CH group, and R stands for straight-chain or branched alkyl having 1 to 6 carbon atoms, straight-chain or branched dialkylaminoalkyl having 1 to 4 carbon atoms in each alkyl group, straight-chain or branched alkenyl having 3 to 6 carbon atoms, straight-chain or branched alkinyl having 3 to 6 carbon atoms, straight-chain or branched alkoxyalkyl having 1 to 6 carbon atoms in the alkyl moiety and 1 to 6 carbon atoms in the alkoxy moiety, or
R stands for aralkyl having 1 to 4 carbon atoms in the alkyl moiety and 6 to 10 carbon atoms in the aryl moiety, where the aryl moiety can be monosubstituted or polysubstituted by identical or different substituents from the series comprising halogen, cyano, nitro, phenyl, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different halogen atoms, such as fluorine, chlorine or bromine atoms, by straight-chain or branched halogenoalkoxy having 1 to 4 carbon atoms, and 1 to 9 identical or different halogen atoms, such as fluorine, chlorine or bromine atoms, and/or by straight-chain or branched halogenoalkylthio having 1 to 4 carbon atoms and 1 to 9 identical or different halogen atoms, such as fluorine, chlorine or bromine atoms, or by a five- or six-membered nitrogen containing heterocyclic ring, linked via N, which can optionally contain further heteroatoms, such as nitrogen, oxygen and/or sulphur, and which can be monosubstituted or polysubstituted by identical or different substituents from the series comprising straight-chain or branched alkyl having 1 to 4 carbon atoms, straight-chain or branched alkoxycarbonyl having 1 to 4 carbon atoms in the alkoxy moiety and/or by alkylcarbamoyl having 1 to 4 carbon atoms in the alkyl moiety, or R stands for aryloxyalkyl having 1 to 4 carbon atoms in the alkyl moiety and 6 to 10 carbon atoms in the aryl moiety, where the aryl moiety can be monosubstituted or polysubstituted by identical or different substituents from the series comprising halogen, cyano, nitro, phenyl, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different halogen atoms, such as fluorine, chlorine or bromine atoms, by straight-chain or branched halogenoalkoxy having 1 to 4 carbon atoms and 1 to 9 identical or different halogen atoms, such as fluorine, chlorine or bromine atoms, and/or by straight-chain or branched halogenoalkylthio having 1 to 4 carbon atoms and 1 to 9 identical or different halogen atoms, such as fluorine, chlorine or bromine atoms, or by a five- or six-membered nitrogen containing heterocyclic ring, linked via N, which can optionally contain further heteroatoms such as nitrogen, oxygen and/or sulphur and which can be monosubstituted or polysubstituted by identical or different substituents from the series comprising straight-chain or branched alkyl having 1 to 4 carbon atoms, straight-chain or branched alkoxycarbonyl having 1 to 4 carbon atoms in the alkoxy moiety and/or alkylcarbamoyl having 1 to 4 carbon atoms in the alkyl moiety, or R stands for aryl having 6 to 10 carbon atoms, where the aryl radical can be monosubstituted or polysubstituted by identical or different substituents from the series comprising halogen, cyano, nitro, phenyl, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different halogen atoms, such as fluorine, chlorine or bromine atoms, by straight-chain or branched halogenoalkoxy having 1 to 4 carbon atoms and 1 to 9 identical or different halogen atoms, such as fluorine, chlorine or bromine atoms, and/or by straight-chain or branched halogenoalkylthio having 1 to 4 carbon atoms and 1 to 9 identical or different halogen atoms, such as fluorine, chlorine or bromine atoms, or by a five- or six-membered nitrogen containing heterocyclic ring, linked via N, which can optionally contain further heteroatoms, such as ntirogen, oxygen and/or sulphur, and which can be monosubstituted or polysubstituted by identical or different substituents from the series comprising straight-chain or branched alkyl having 1 to 4 carbon atoms, straight-chain or branched alkoxycarbonyl having 1 to 4 carbon atoms in the alkoxy moiety and/or by alkylcarbamoyl having 1 to 4 carbon atoms in the alkyl moiety, or R stands for a radical of the formula

wherein $R^1$ stands for hydrogen, straight-chain or branched alkyl having 1 to 6 carbon atoms, straight-chain or branched alkenyl having 2 to 6 carbon atoms, straight-chain or branched alkinyl having 2 to 6 carbon atoms or for cycloalkyl having 3 to 7 carbon atoms, and $R^2$ stands for hydrogen, straight-chain or branched alkyl having 1 to 16 carbon atoms, straight-chain or branched alkoxyalkyl having 1 to 4 carbon atoms in the alkyl part and 1 to 4 carbon atoms in the alkoxy part, straight-chain or branched alkenyl having 2 to 6 carbon atoms, straight-chain or branched alkinyl having 2 to 6 carbon atoms, cycloalkyl having 3 to 7 carbon atoms, cycloalkylalkyl having 3 to 7 carbon atoms in the cycloalkyl part and 1 to 4 carbon atoms in the alkyl part, or for phenyl which can be monosubstituted or polysubstituted by identical or different substituents from the series comprising halogen, in particular fluorine, chlorine and bromine, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different halogen atoms, such as fluroine, chlorine or bromine atoms, by straight-chain or branched halogenoalkoxy having 1 to 4 carbon atoms and 1 and 9 identical or different halogen atoms, such as fluorine, chlorine or bromine atoms, and/or by straight-chain or branched halogenoalkylthio having 1 to 4 carbon atoms and 1 to 9 identical or different halogen atoms, such as fluorine, chlorine or bromine atoms, or $R^2$ stands for aralkyl having 1 to 4 carbon atoms in the alkyl moiety and 6 to 10 carbon atoms in the aryl moiety, wherein the aryl moiety can be monosubstituted or polysubstituted by identical or different substituents from the series comprising halogen, in particular fluorine, chlorine and bromine, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different halogen atoms, such as fluorine, chlorine or bromine atoms, by straight-chain or branched halogenoalkoxy having 1 to 4 carbon atoms and 1 to 9 identical or different halogen atoms, such as fluorine, chlorine or bromine atoms, and/or by straight-chain or branched halogenoalkylthio having 1 to 4 carbon atoms and 1 to 9 identical or different halogen atoms, such as fluorine, chlorine or bromine atoms, or $R^1$ and $R^2$ together with the nitrogen atom to which they are bonded stand for a saturated 5 to 7-membered heterocyclic ring, where the heterocyclic ring can contain a further heteroatom, such as nitrogen, oxygen or sulphur, and where the heterocyclic ring can be monosubstituted or polysubstituted by identical or different substituents from the series comprising straight-chain or branched alkyl having 1 to 4 carbon atoms, straight-chain or branched hydroxyalkyl having 1 to 4 carbon atoms, straight-chain or branched alkanoyl having 1 to 4 carbon atoms in the alkane moiety and/or by alkanoyloxyalkyl having 1 to 4 carbon atoms in the alkane moiety and 1 to 4 carbon atoms in the oxyalkyl moiety.

Particularly preferred compounds of the formula (I) are those in which

Ar stands for phenyl which can be monosubstituted, disubstituted or trisubstituted by identical or different substituents from the series comprising fluorine, chlorine, bromine, methyl, ethyl, n- or i-propyl, n-, i-, s- or t-butyl, methoxy, ethoxy, n- or i-propoxy, methylthio, trifluoromethyl, trifluoromethoxy or trifluoromethylthio, Z stands for nitrogen or a CH group and R stands for methyl, ethyl, n- or i-propyl, n-, i-, s- or t-butyl, dimethylaminopropyl, allyl, n- or i-butenyl, propargyl, methoxymethyl, methoxyethyl, ethoxymethyl, ethoxyethyl, n- or i-propoxymethyl, n- or i-propoxyethyl, or for benzyl, phenylethyl, phenoxymethyl or phenyl, where each of these benzyl, phenylethyl, phenoxymethyl or phenyl radicals can be monosubstituted, disubstituted or trisubstituted by identical or different substituents from the series comprising fluorine, chlorine, bromine, methyl, ethyl, n- or i-propyl, n-, i-, s- or t-butyl, methoxy, ethoxy, n- or i-propoxy, methylthio, trifluoromethyl, trifluoromethoxy, trifluoromethylthio, phenyl, triazolyl which is optionally monosubstituted, disubstituted or trisubstituted by identical or different substituents from the series comprising methyl, ethyl, methoxycarbonyl, ethoxycarbonyl, methylcarbamoyl or ethylcarbamoyl, imidazolyl which is optionally monosubstituted, disubstituted or trisubstituted by identical or different substituents from the series comprising methyl, ethyl, methoxycarbonyl, ethoxycarbonyl, methylcarbamoyl or ethylcarbamoyl, pyrazolyl which is optionally monosubstituted, disubstituted or trisubstituted by identical or different substituents from the series comprising methyl, ethyl, methoxycarbonyl, ethoxycarbonyl, methylcarbamoyl or ethylcarbamoyl, pyrrolidinyl which is optionally monosubstituted, disubstituted or trisubstituted by identical or different substituents from the series comprising methyl, ethyl, methoxycarbonyl, ethoxycarbonyl, methylcarbamoyl or ethylcarbamoyl, piperidinyl which is optionally monosubstituted, disubstituted or trisubstituted by identical or different substituents from the series comprising methyl, ethyl, methoxycarbonyl, ethoxycarbonyl, methylcarbamoyl or ethylcarbamoyl, morpholinyl which is optionally monosubstituted, disubstituted or trisubstituted by identical or different substituents from the series comprising methyl, ethyl, methoxycarbonyl, ethoxycarbonyl, methylcarbamoyl or ethylcarbamoyl and/or piperazinyl which is optionally monosubstituted, disubstituted or trisubstituted by identical or different substituents from the series comprising methyl, ethyl, methoxycarbonyl, ethoxycarbonyl, methylcarbamoyl or ethylcarbamoyl, or R stands for a radical of the formula

wherein $R^1$ stands for hydrogen, methyl, ethyl, n- or i-propyl, n-, i-, s- or t-butyl, allyl, n- or i-butenyl, propargyl, n- or i-butinyl, cyclopentyl or cyclohexyl and $R^2$ stands for hydrogen, methyl, ethyl, n- or i-propyl, n-, i-, s- or t-butyl, hexyl or n-dodecyl, methoxymethyl, methoxyethyl, ethoxymethyl, ethoxyethyl, methoxypropyl, ethoxypropyl, allyl, n- or i-butenyl, propargyl, n- or i-butinyl, cyclopentyl, cyclohexyl, cyclopentylmethyl, cyclohexylmethyl, or for phenyl which can be monosubstituted, disubstituted or trisubstituted by identical or different substituents from the series comprising fluorine, chlorine, bromine, methyl, ethyl, n- or i-propyl, n-, i-, s- or t-butyl, methoxy, ethoxy, n- or i-propoxy, methylthio, trifluormethyl, trifluormethoxy and/or trifluoromethylthio, or $R^2$ stands for benzyl or phenethyl, wherein each of these radicals can be monosubstituted, disubstituted or trisubstituted in the phenyl part by identical or different substituents from the series comprising fluorine, chlorine, bromine, methyl, ethyl, n- or i-propyl, n-, i-, s- or t-butyl, methoxy, ethoxy, n- or i-propoxy, methylthio, trifluoromethyl, trifluoromethoxy and/or trifluoromethylthio, or $R^1$ and $R^2$ together with nitrogen atom to which they are bonded stand for pyrrolidinyl, piperidinyl, hexahydroazephinyl, morpholinyl, thiamorpholinyl or 1,4-piperazinyl, where each of the mentioned radicals can be monosubstituted, disubstituted or trisubstituted by identical or different substituents from the series comprising methyl, ethyl, hydroxymethyl, acetyl, propionyl and/or acetoxymethyl.

Very particularly preferred compounds of the formula (I) are those in which

Ar stands for phenyl which is optionally monosubstituted or disubstituted by identical or different substituents from the series comprising fluorine, chlorine, bromine, methyl, methoxy, trifluoromethyl, trifluoromethoxy and/or trifluoromethylthio, Z stands for nitrogen or a CH group and R stands for methyl, ethyl, n-propyl, isopropyl, n-, i-, s- or t-butyl, dimethylaminopropyl, allyl, propargyl, methoxymethyl, benzyl, phenoxymethyl or phenyl, where each of these benzyl, phenoxymethyl and phenyl radicals can be monosubstituted or disubstituted by identical or different substituents from the series comprising fluorine, chlorine, bromine, methyl, methoxy, trifluoromethyl, trifluoromethoxy, trifluoromethylthio and/or phenyl, or by triazolyl which is optionally monosubstituted or disubstituted by identical or different substituents from the series comprising methyl, methoxycarbonyl, ethoxycarbonyl or methylcarbamoyl, imidazolyl which is optionally monosubstituted or disubstituted by identical or different substituents from the series comprising methyl, methoxycarbonyl, ethoxycarbonyl, or methylcarbamoyl, pyrazolyl which is optionally monosubstituted or disubstituted by identical or different substituents from the series comprising methyl, methoxycarbonyl, ethoxycarbonyl or methylcarbamoyl, piperidinyl which is optionally monosubstituted or disubstituted by identical or different substituents from the series comprising methyl, methoxycarbonyl, ethoxycarbonyl or methylcarbamoyl, morpholinyl which is optionally monosubstituted or disubstituted by identical or different substituents from the series comprising methyl, methoxycarbonyl, ethoxycarbonyl or methylcarbamoyl or piperazinyl which is optionally monosubstituted or disubstituted by identical or different substiutuents from the series comprising methyl, methoxycarbonyl, ethoxycarbonyl or methylcarbamoyl, or R stands for radical of the formula

wherein $R^1$ stands for hydrogen, methyl, eethyl, n- or i-propyl or cyclohexyl, $R^2$ stands for hydrogen, methyl, ethyl, n- or i-propyl, i-butyl, n-butyl, n-hexyl or n-dodecyl, methoxymethyl, methoxyethyl, methoxypropyl, ethoxymethyl, ethoxyethyl, allyl, cyclohexyl, cyclopentylmethyl, cyclohexylmethyl or for phenyl which is optionally monosubstituted or disubstituted by identical or different substituents from the series comprising fluorine, chlorine, bromine, methyl, methoxy, trifluoromethyl, trifluoromethoxy and/or trifluoromethylthio, or $R^2$ stands for benzyl or phenylethyl, wherein each of these radicals can be monosubstituted or disubstituted in the phenyl part by identical or different substituents from the series comprising fluorine, chlorine, bromine, methyl, methoxy, trifluoromethyl, trifluoromethoxy and/or trifluoromethylthio, or $R^1$ and $R^2$ together with the nitrogen atom to which they are bonded stand for pyrrolidinyl which is optionally monosubstituted, disubstituted or trisubstituted by methyl, piperidinyl which is optionally monosubstituted, disubstituted or trisubstituted by methyl, morpholinyl which is optionally monosubstituted, disubstituted or trisubstituted by methyl, or 1,4-piperazinyl which is optionally substituted on the nitrogen by methyl, ethyl, acetyl or propionyl.

Preferred compounds according to the invention are also addition products of acids and those substituted azolylmethylcarbinols of the formula (I) in which the substituents Ar, R and Z have the meanings which have already been mentioned as preferred for these substituents.

The acids which can be subjected to the addition reaction preferably include hydrohalic acids, such as, for example, hydrochloric acid and hydrobromic acid, in particular hydrochloric acid, furthermore phosphoric acid, nitric acid, sulphuric acid, mono-, bi- and trifunctional carboxylic acids and hydroxycarboxylic acids, such as, for example, acetic acid, maleic acid, succinic acid, fumaric acid, tartaric acid, citric acid, salicylic acid, sorbic acid and lactic acid, sulphonic acids, such as, for example, p-toluenesulphonic acid and 1,5-naphthalenedisulphonic acid, and also saccharin or thiosaccharin.

Additionally preferred compounds according to the invention are addition products of salts of metals of main groups II to IV and subgroups I and II and IV to VIII of the periodic table of the elements and those substituted azolylmethylcarbinols of the formula (I) in which the substituents Ar, R and Z have the meanings which have already been mentioned as preferred for these substituents.

In these addition products, salts of copper, zinc, manganese, magnesium, tin, iron and of nickel are particularly preferred. Suitable anions of these salts are those which are derived from acids leading to addition products tolerated by plants. In this context, acids of this type which are particularly preferred are the hydrohalic acids, such as, for example, hydrochloric acid and hydrobromic acid, nitric acid and sulphuric acid.

In addition to the compounds mentioned in the preparation examples, the following substituted azolylmethylcarbinols of the general formula (I) may be mentioned individually:

TABLE 1

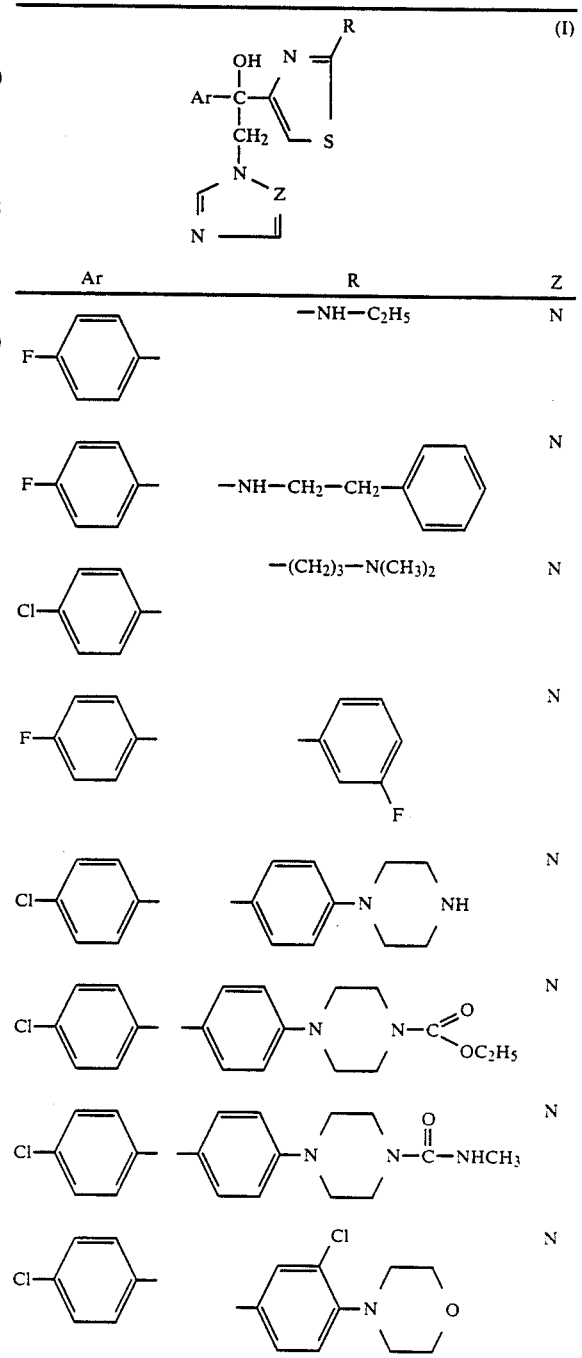

TABLE 1-continued

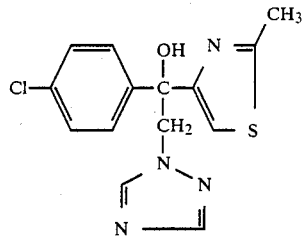

| Ar | R | Z |
|---|---|---|
| 4-Cl-C₆H₄— | 3,5-dimethylpiperidin-1-yl-phenyl | N |
| 4-Cl-C₆H₄— | 2-Cl, 3-methylpiperidin-1-yl-phenyl | N |
| 4-Cl-C₆H₄— | 2-Cl, pyrazol-1-yl-phenyl | N |
| 3,4-F₂-C₆H₃— | —(CH₂)₃—CH₃ | N |
| 3,4-F₂-C₆H₃— | —(CH₂)₂—CH₃ | N |

If, for example, 1-(4-chlorophenyl)-1-(2-methylthiazol-4-yl)-2-bromoethanol and 1,2,4-triazole are used as starting substances, the course of the reaction of the process according to the invention may be represented by the following equation:

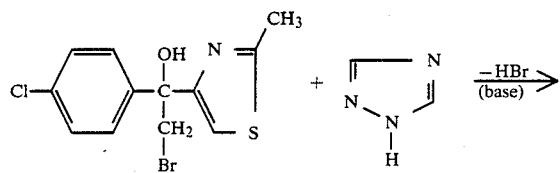

Formula (II) provides a general definition of the substituted 2-bromoethanols required as starting substances for carrying out the process according to the invention. In this formula (II) Ar and R preferably stand for those radicals which have already been mentioned in connection with the description of the substances of the formula (I) according to the invention as being preferred for these substituents.

The substituted 2-bromoethanols of the formula (II) were hitherto unknown. They are obtained when dibromoacyloins of the formula

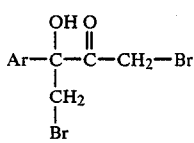

in which
Ar has the abovementioned meaning
are reacted with thiocarboxamides of the formula

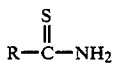

in which
R has the abovementioned meaning,
initially in the presence of a base, such as sodium hydrogen carbonate, and in the presence of a diluent, such as ethanol, and the reaction product is then reacted in the presence of an acid, such as p-toluenesulphonic acid, and in the presence of a diluent, such as dichloromethane, at temperatures between 0° C. and 60° C. (cf. also preparation examples).

Dibromoacyloins of the formula (IV) are known (cf. Helvetica Chim. Acta 29, 95–101 [1946]). They can be prepared by reacting dibromodiacetyl (cf. Liebigs Ann. Chem. 249, 207 [1888]) with aromatic compounds of the formula

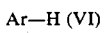

in which
Ar has the abovementioned meaning,
in customary manner by Friedel-Crafts reaction in the presence of a catalyst, such as aluminum (III) chloride, at temperatures between 0° C. and 80° C. (cf. also preparation examples).

Thiocarboxamides of the formula (V) and aromatic compounds of the formula (VI) are generally known compounds of organic chemistry.

Formula (III) provides a general definition of the azoles furthermore required as starting substances for carrying out the process according to the invention. In this formula (III), Z preferably stands for those radicals which have already been mentioned in connection with the description of the substances of the formula (I) according to the invention as being preferred for this substituent.

The azoles of the formula (III) are also generally known compounds of organic chemistry.

Suitable diluents for carrying out the process according to the invention are inert organic solvents. These include in particular aliphatic, alicyclic or aromatic hydrocarbons, such as, for example, benzine, benzene, toluene, xylene, petroleum ether, hexane, cyclohexane, ethers, such as diethyl ether, dioxane, tetrahydrofuran or ethylene glycol dimethyl ether or ethylene glycol diethyl ether, nitriles, such as acetonitrile or propionitrile, amides, such as dimethylformamide, dimethylacetamide, N-methylformanilide, N-methylpyrrolidone or hexamethylphosphoric triamide, or sulphoxides, such as dimethyl sulphoxide, or alcohols, such as methanol, ethanol, propanol or butanol.

The process according to the invention is preferably carried out in the presence of a suitable reaction auxiliary. Suitable as such are all customarily utilizable inorganic and organic bases. The hydrides, hydroxides, amides, alkoxides, carbonates or hydrogen carbonates of alkali metals, such as, for example sodium hydride, sodium amide, sodium hydroxide, sodium methoxide, sodium ethoxide, potassium t-butoxide, sodium carbonate or sodium hydrogen carbonate, or also tertiary amines, such as, for example, triethylamine, N,N-dimethylaniline, pyridine, N,N-dimethylaminopyridine, diazabicyclooctane (DABCO), diazabicyclononene (DBN) or diazabicycloundecene (DBU), are preferably used.

If appropriate, the process according to the invention can also be carried out in a two-phase system, such as, for example, water/toluene, if appropriate in the presence of a phase transfer catalyst. Examples of such catalysts which may be mentioned are: tetrabutylammonium iodide, tetrabutylammonium bromide, tributylmethylphosphonium bromide, trimethyl-$C_{13}$/$C_{15}$-alkylammonium chloride, dibenzyl-dimethylammoniummethyl sulphate, dimethyl-$C_{12}$/$C_{14}$-alkylbenzylammonium chloride, tetrabutylammonium hydroxide, 15-crown-5, 18-crown-6, triethylbenzylammonium chloride and trimethylbenzylammonium chloride.

When carrying out the process according to the invention, the reaction temperatures may be varied within a relatively wide range. In general, the process is carried out at temperatures between 20° C. and 200° C., preferably at temperatures between 40° C. and 140° C.

1.0 to 2.0 moles, preferably 1.0 to 1.5 moles, of azole of the formula (III) and 1.0 to 2.0 moles, preferably 1.0 to 1.5 moles, of reaction auxiliary are generally employed per mole of substituted 2-bromoethanol of the formula (II) when carrying out the process according to the invention. The reaction is carried out and the reaction products worked up and isolated by generally customary methods.

The compounds of the formula (I) which are obtainable by the process according to the invention can be converted into acid addition salts or metal salt complexes.

Suitable acids for the preparation of acid addition salts of the compounds of the formula (I) are preferably those which have already been mentioned in connection with the description of the acid addition salts according to the invention as being preferred acids.

The acid addition salts of the compounds of the formula (I) can be obtained in a simple manner by customary salt formation methods, for example, by dissolving a compound of the formula (I) in a suitable inert solvent and by adding the acid, for example hydrochloric acid, and they can be isolated in a known manner, for example by filtering off, and purified, if appropriate, by washing with an inert organic solvent.

Suitable metal salts for the preparation of metal salt complexes of the compounds of the general formula (I) are preferably those which have already been described above.

The metal salt complexes of compounds of the formula (I) can be obtained in a simple manner by customary methods, for example by dissolving the metal salt in alcohol, for example ethanol, and adding the solution to compounds of the formula (I). Metal salt complexes can be isolated in a known manner, for example by filtering off and, if appropriate, purified by recrystallization.

The active compounds according to the invention exhibit a strong microbicidal action and can be employed as fungicides for combating undesired microorganisms.

Fungicidal agents in plant protection are employed for combating Plasmodiophoromycetes, Oomycetes, Chytridiomycetes, Zygomycetes, Ascomycetes, Basidiomycetes and Deuteromycetes.

Some pathogens of fungal diseases which come under the generic names listed above may be mentioned as examples, but not by way of limitation: Pythium species, such as, for example, *Pythium ultimum*; Phytophthora species, such as, for example, *Phytophthora infestans*; Pseudoperonospora species, such as, for example, *Pseudoperonospora humuli* or *Pseudoperonospora cubensis*; Plasmopara species, such as, for example, *Plasmopara viticola*; Peronospora species, such as, for example, *Peronospora pisi* or *P. brassicae*; Erysiphe species, such as, for example, *Erysiphe graminis*; Sphaerotheca species, such as, for example, *Sphaerotheca fuliginea*; Podosphaera species, such as, for example, *Podosphaera Leucotricha*; Venturia species, such as, for example, *Venturia inaequalis*; Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus*; Puccinia species, such as, for example, *Puccinia recondita*; Tilletia species, such as, for example, *Tilletia caries*; Ustilago species, such as, for example, *Ustilago nuda* or *Ustilago avenae*; Pellicularia species, such as, for example, *Pellicularia sasakii*; Pyricularia species, such as, for example, *Pyricularia oryzae*; Fusarium species, such as, for example, *Fusarium culmorum*; Botrytis species, such as, for example, *Botrytis cinerea*; Septoria species, such as, for example, *Septoria nodorum*; Leptosphaeria species, such as, for example, *Leptosphaeria nodorum*; Cercospora species, such as, for example, *Cercospora canescens*; Alternaria species, such as, for example, *Alternaria brassicae* and Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

In this field of application, the active compounds according to the invention can be employed with particularly good success for combating cereal diseases, such as, for example, against the pathogen of stem break in cereals (*Pseudocercosporella herpotrichoides*) or against the pathogen of net blotch of barley (*Pyrenophora teres*) or against the pathogen of spot blotch of wheat (*Cochliobolus sativus*) or against the pathogen of leaf spot of wheat (*Lepthosphaeria nodorum*), against mildews, and for combating diseases in fruit and vegetable growing, such as, for example, against the pathogen of powdery mildew of curcurbits (*Sphaerotheca fuliginea*) or against the pathogen of apple scab (*Venturia inaequalis*), against Cercospora and Uromyces species, such as, for example, against the pathogen of bean rust (*Uromyces appendiculatus*), and for combating rice diseases, such as, for example, against the pathogen of blast disease of rice (*Pyricularia oryzae*).

In the preservation of materials, the active compounds according to the invention can be used to preserve industrial materials. Industrial materials in this connection are to be understood as non-living materials which have been prepared for use in industry. Industrial materials which are to be protected from microbial change or destruction by the active compounds according to the invention can be, for example, adhesives, sizes, paper, card, textiles, leather, wood, paints, articles made of plastic, cooling lubricants and other materials which can be attacked or decomposed by microorganisms. In the context of the materials to be preserved, components of production lines, for example cooling water circulations, which can be impaired by multiplication of microorganisms, may also be mentioned. Industrial materials which may be mentioned as preferred in the context of the present invention are adhesives, sizes, paper and card, leather, wood, paints, cooling lubricants and cooling circulations, particularly preferably wood.

Examples which may be mentioned of microorganisms which can cause degradation to or a change in the industrial materials are bacteria, fungi, yeasts, algae and slime organisms. The active compounds according to the invention preferentially act against fungi, in particular moulds, fungi which discolour and destroy wood (Basidiomycetes), and against slime organisims and algae.

The active compounds according to the invention furthermore engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the corp plants in the particular manner desired.

Plant growth-regulating compounds can be employed, for example, to inhibit vegetative growth of the plants. Such inhibition of growth is, inter alia, of economic interest in the case of grasses, since it is thereby possible to reduce the frequency of cutting the grass in ornamental gardens, parks and sports grounds, on verges, at airports or in fruit orchards. The inhibition of growth of herbaceous and woody plants on verges and in the vicinity of pipelines or overland lines or, quite generally, in areas in which heavy additional growth of plants is undesired, is also of importance.

The use of growth regulators to inhibit the growth in length of cereals is also important. The danger of bending ("lodging") of the plants before harvesting is thereby reduced or completely eliminated. Furthermore, growth regulators can strengthen the stem of cereals, which again counteracts lodging. The use of growth regulators for shortening and strengthening the stem enables higher amounts of fertiliser to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beet, sugar cane, pineapples and citrus fruit or to increase the protein content in soybeans or cereals. Using growth regulators it is also possible, for example, to inhibit the degradation of desired constituents, such as, for example, sugar in sugar beet or sugar cane, before or after harvesting. It is also possible favourably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can also be promoted up to a certain degree ("thinning out") in order to interrupt the alternance. By alternance there is understood the peculiarity of some varieties of fruit to produce very different yields from year to year, for endogenic reasons. Finally, using growth regulators it is possible to reduce the force required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usually unsuitable for this purpose thereby becomes possible.

Depending on their particular physical and/or chemical properties, the active compounds can be converted into the customary formulations, such as solutions, emulsions, suspensions, powders, foams, pastes, granules, aerosols, very fine capsules in polymeric substances and in coating compositions for seed, and ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvent. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant those liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol, polyvinyl acetate and natural phospholipids, such as cephalins and lecithins, and synthetic phospholipids, can be used in the formulations. Further additives may be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and also in mixtures with fertilizers and growth regulators.

The active compounds can be used as such, in the form of their formulations or as the use forms prepared therefrom, such as ready-to-use solutions, suspensions, wettable powders, pastes, soluble powders, dusting agents and granules. They are used in the customary manner, for example by watering, spraying, atomizing, scattering, dusting, foaming, coating and the like. It is furthermore possible to apply the active compounds in accordance with the ultra-low volume process or to inject the active compound preparation or the active compound itself into the soil. It is also possible to treat the seeds of plants.

When the substances according to the invention are employed as fungicides, the application rate can be varied within a relatively wide range, depending on the method of application. For example, the concentrations of active compound in the treatment of parts of plants are generally between 1 and 0.0001% by weight, preferably between 0.5 and 0.001%, in the use forms. In the treatment of seed, amounts of active compound of 0.001 to 50 g per kilogram of seed, preferably 0.01 to 10 g, are generally required. In the treatment of the soil, concentrations of active compound of 0.00001 to 0.1% by weight, preferably of 0.0001 to 0.02%, are required at the site of action.

If the compounds according to the invention are employed as plant growth regulators, the application rates can be varied within a relatively wide range. In general, 0.01 to 50 kg, preferably 0.05 to 10 kg, of active compound are employed per hectare of soil surface.

If the substances according to the invention are employed as plant growth regulators, the rule is that the application is carried out within a preferred period of time, the exact definition of which depends on the climatic and vegetative circumstances.

The preparation and the use of the active compounds according to the invention are evident from the examples which follow.

PREPARATION EXAMPLES

EXAMPLE 1

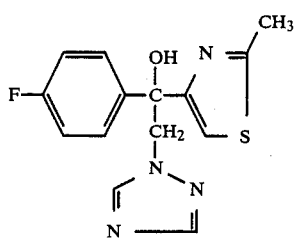

At 10° C., a solution of 4.1 g (0.06 mol) of 1,2,4-triazole in 30 ml of dimethylformamide is added dropwise and with stirring to a suspension of 1.8 g (0.06 mol) of sodium hydride in 20 ml of dimethylformamide, and, after an hour, a solution of 12.6 g (0.04 mol) of 2-bromo-1-(4-fluorophenyl)-1-(2-methylthiazol-4-yl)-ethanol in 30 ml of dimethylformamide is likewise added dropwise at 0° C. and with stirring. When the addition is complete, the mixture is stirred for an hour at 20° C., for a further two hours at 70° C., for two hours at 90° C. and for a further hour at 110° C. For working up, the reaction mixture is cooled and evaporated in vacuo, the residue is taken up in 300 ml of dichloromethane, the solution is washed twice using 200 ml of water each time, dried over sodium sulphate and concentrated in vacuo the residue is chromatographed over silica gel (eluent: dichloromethane/methanol 10:1), and the product thus obtained is crystallized by stirring with 150 ml of diisopropyl ether. 3.5 g (29% of theory) of 1-(4-fluorophenyl)-1-(2-methylthiazol-4-yl)-2-(1,2,4-triazol-1-yl)-ethanol of melting point 120° C. are obtained.

PREPARATION OF THE STARTING COMPOUND

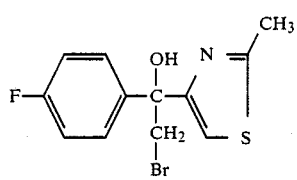
(II-1)

A solution of 51 g (0.15 mol) of 1,4-dibromo-3-(4-fluorophenyl)-3-hydroxy-butan-2-one in 200 ml of ethanol is added dropwise and with stirring to 11.3 g (0.15 mol) of thioacetamide in 100 ml of ethanol, during which the temperature of the reaction mixture increases to 35° C. 12.6 g (0.15 mol) of sodium hydrogen carbonate are then added, the mixture is stirred for 18 hours at room temperature and then evaporated in vacuo, the residue is taken up in 600 ml of dichloromethane and washed twice using 200 ml of water each time, 5.7 g (0.03 mol) of p-toluenesulphonic acid are added to the mixture, and the latter is refluxed for 24 hours over a water separator. For working up, the reaction mixture is washed twice using 200 ml of water each time, the organic phase is dried over sodium sulphate and evaporated in vacuo, and the residue is chromatographed over silica gel (eluent:toluene).

28.5 g (60% of theory) of 2-bromo-1-(4-fluorophenyl)-1-(2-methylthiazol-4-yl)-ethanol are obtained as an oil of refractive index $n_D^{20}$ 1.5812.

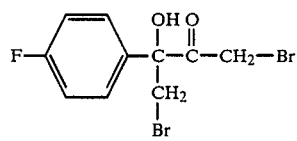
(IV-1)

In the course of 2 hours, 122 g (0.5 mol) of 1,4-dibromobutane-2,3-dione are added in portions to 133 g (1 mol) of aluminum (III) chloride in 1 l of fluorobenzene, during which the temperature of the reaction mixture increases to 30° C. When the addition is complete, the reaction mixture is warmed slowly to 70° C., stirred at this temperature for 2 hours and cooled, and the reaction batch is added at 0° C. to 3 l of 0.2N hydrochloric acid. For working up, the aqueous phase is separated off and extracted using 300 ml of toluene. The combined organic phases are washed three times using 500 ml of water each time, dried over sodium sulphate and evaporated in vacuo. The residue is crystallized using 75 ml of diisopropyl ether.

87.5 g (52% of theory) of 1,4-dibromo-3-(4-fluorophenyl)-3-hydroxybutan-2-one of melting point 90° C. are obtained.

In a corresponding manner and in accordance with the general instructions for the preparation, the substituted azolylmethylcarbinols of the formula (I) listed in the following table are obtained.

TABLE 2
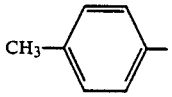
| Example No. | Ar | R | Z | Melting point [°C.] |
|---|---|---|---|---|
| 2 | 4-CH₃-C₆H₄- | 4-Cl-C₆H₄- | N | 208 |
| 3 | 4-CH₃-C₆H₄- | 4-Cl-C₆H₄- | CH | 228 |
| 4 | 4-CH₃-C₆H₄- | morpholino | N | 136 |
| 5 | 4-CH₃-C₆H₄- | morpholino | CH | 156 |
| 6 | 4-CH₃-C₆H₄- | 4-Cl-C₆H₄-CH₂- | N | 104 |
| 7 | 4-CH₃-C₆H₄- | 4-Cl-C₆H₄-CH₂- | CH | 122 |
| 8 | 4-Cl-C₆H₄- | morpholino | N | 150 |
| 9 | 4-Cl-C₆H₄- | morpholino | CH | 188 |
| 10 | 4-CH₃-C₆H₄- | 4-Cl-C₆H₄-O-CH₂- | N | 139 |
| 11 | 4-CH₃-C₆H₄- | 4-Cl-C₆H₄-O-CH₂- | CH | 138 |
| 12 | C₆H₅- | morpholino | CH | 160 |

TABLE 2-continued
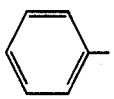 (I)
| Example No. | Ar | R | Z | Melting point [°C.] |
|---|---|---|---|---|
| 13 | 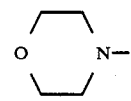 |  | N | 158 |
| 14 | 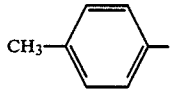 | 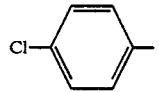 | CH | 208 |
| 15 | 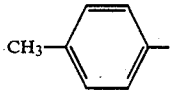 | 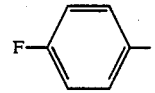 | N | 150 |
| 16 | 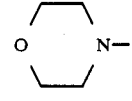 |  | CH | 142 |
| 17 | 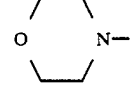 | 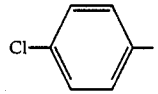 | N | 130 |
| 18 | 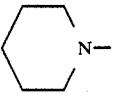 | 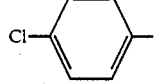 | CH | 174 |
| 19 | 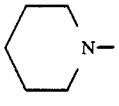 | 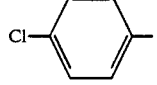 | N | 169 |
| 20 | 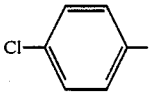 | 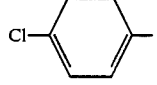 | CH | 230 |
| 21 | 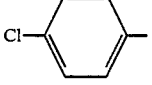 | 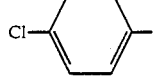 | N | 168 |
| 22 | 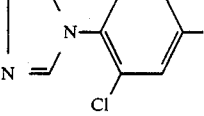 |  | CH | 200 |

TABLE 2-continued
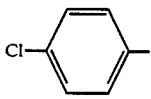
(I)
| Example No. | Ar | R | Z | Melting point [°C.] |
|---|---|---|---|---|
| 23 | 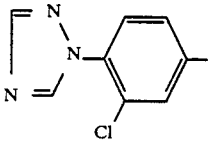 4-Cl-C6H4 | 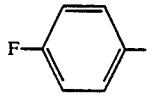 | N | 154 |
| 24 | 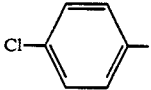 4-F-C6H4 | CH3 | CH | 196 |
| 25 | 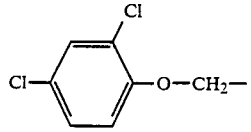 4-Cl-C6H4 | 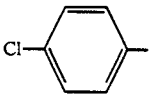 2,4-Cl2-C6H3-O-CH2- | CH | 136 |
| 26 | 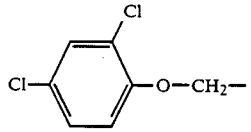 4-Cl-C6H4 | 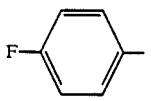 2,4-Cl2-C6H3-O-CH2- | N | 110 |
| 27 | 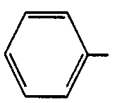 4-F-C6H4 | 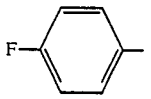 C6H5 | CH | 149 |
| 28 | 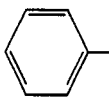 4-F-C6H4 |  C6H5 | N | 126 |
| 29 | 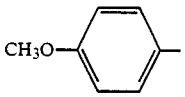 4-Cl-C6H4 | 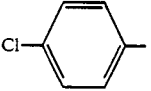 4-CH3O-C6H4 | CH | 205 |
| 30 | 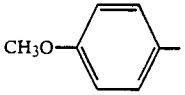 4-Cl-C6H4 | 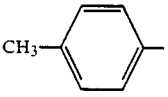 4-CH3O-C6H4 | N | 158 |
| 31 | 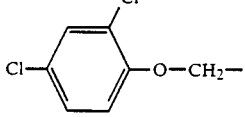 4-CH3-C6H4 | 2,4-Cl2-C6H3-O-CH2- | N | 115 |
| 32 |  4-F-C6H4 | $(CH_3)_2N-$ | CH | 148 |

TABLE 2-continued $$\text{(I)}$$

Structure (I): Ar-C(OH)(CH₂-N(-N=CH-Z=CH-)-)-CH=C(S-)-N=C(R)- (triazole/tetrazole-thione system as depicted)

| Example No. | Ar | R | Z | Melting point [°C.] |
|---|---|---|---|---|
| 33 | 4-F-C₆H₄- | (CH₃)₂N— | N | 130 |
| 34 | 4-CH₃-C₆H₄- | 2,4-diCl-C₆H₃-O-CH₂— | CH | 96 |
| 35 | 4-Cl-C₆H₄- | 3-CH₃-C₆H₄- | CH | 182 |
| 36 | 4-Cl-C₆H₄- | 3-CH₃-C₆H₄- | N | 123 |
| 37 | 4-Cl-C₆H₄- | CH₃—NH— | N | 148 |
| 38 | 4-Cl-C₆H₄- | CH₃—NH— | CH | 176 |
| 39 | 4-F-C₆H₄- | 4-Cl-C₆H₄- | CH | 225 |
| 40 | 4-F-C₆H₄- | 4-Cl-C₆H₄- | N | 145 |
| 41 | 4-Cl-C₆H₄- | 4-F-C₆H₄- | N | 130 |
| 42 | 4-Cl-C₆H₄- | 4-(1,2,4-triazol-1-yl)-C₆H₄- | N | 164 |

TABLE 2-continued
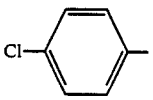
(I)
| Example No. | Ar | R | Z | Melting point [°C.] |
|---|---|---|---|---|
| 43 | 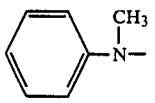 | 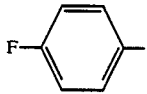 | N | 115 |
| 44 |  | 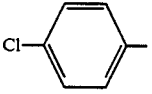 | N | 110 |
| 45 | 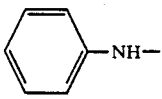 | 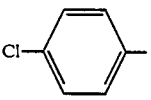 | N | 185 |
| 46 | 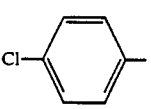 | CH$_2$=CH—CH$_2$—NH— | N | 126 |
| 47 | 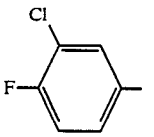 | 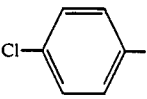 | N | 140 |
| 48 | 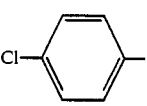 | CH$_2$=CH—CH$_2$—N(C$_2$H$_5$)— | N | 80 |
| 49 | 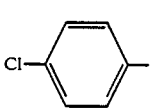 | (C$_2$H$_5$)$_2$N— | N | 116 |
| 50 | 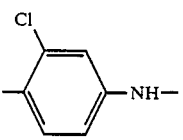 | 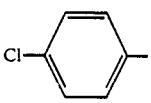 | N | 140 |
| 51 | 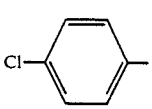 | C$_2$H$_5$—NH— | N | 124 |
| 52 | 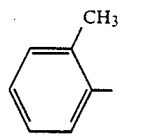 | | N | 110 |

TABLE 2-continued
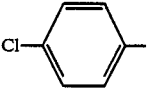
(I)
| Example No. | Ar | R | Z | Melting point [°C.] |
|---|---|---|---|---|
| 53 | 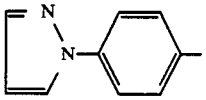 | 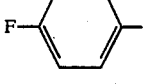 | N | 170 |
| 54 | 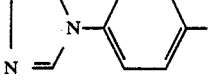 | 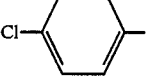 | N | 152 |
| 55 | 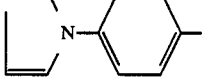 | 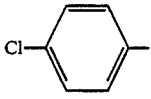 | N | 146 |
| 56 | 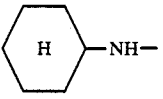 | 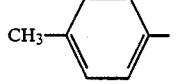 | N | 175 |
| 57 | 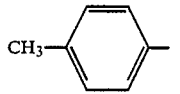 | CH$_3$ | N | 150 |
| 58 | 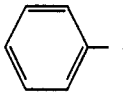 |  | N | 142 |
| 59 |  |  | N | 150 |
| 60 | 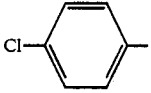 | (CH$_2$)$_2$N— | N | 142 |
| 61 | 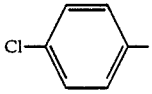 | (CH$_3$)$_2$N— | N | 130 |
| 62 | 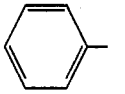 | 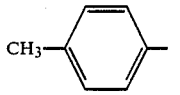 | CH | 171 |
| 63 | CH$_3$-C$_6$H$_4$- | (CH$_3$)$_2$N— | CH | 163 |

TABLE 2-continued
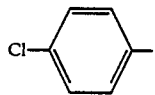
(I)
| Example No. | Ar | R | Z | Melting point [°C.] |
|---|---|---|---|---|
| 64 |  | (CH₃)₂N— | CH | 177 |
| 65 | 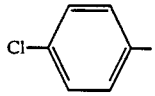 | CH₃ | N | 106 |
| 66 | 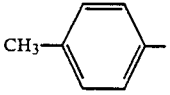 | CH₃ | CH | 182 |
| 67 | 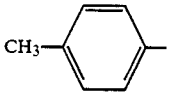 | CH₃ | CH | 160 |
| 68 | 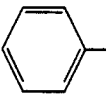 | 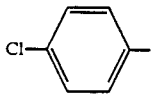 | CH | 165 |
| 69 | 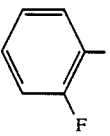 |  | N | 112 |
| 70 | 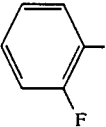 |  | N | 110 |
| 71 | 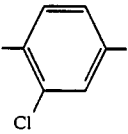 | 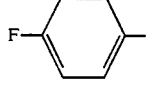 | N | 128 |
| 72 | 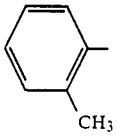 | 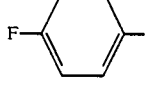 | N | 111 |
| 73 | 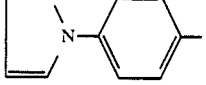 | | N | 200 |

TABLE 2-continued
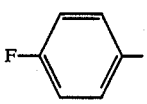
(I)
| Example No. | Ar | R | Z | Melting point [°C.] |
|---|---|---|---|---|
| 74 | 4-F-C₆H₄— | 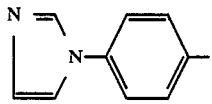 | N | 162 |
| 75 | 4-F-C₆H₄— | 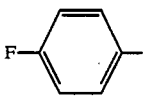 | N | 158 |
| 76 | 4-CH₃-C₆H₄— | 2,4-Cl₂-C₆H₃— | N | 175 |
| 77 | 4-Cl-C₆H₄— | 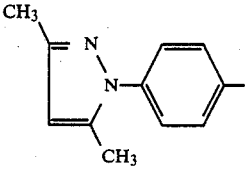 2-OCH₃-C₆H₄—NH— | N | 186 |
| 78 | 4-Cl-C₆H₄— | C₂H₅ | N | 100 |
| 79 | 4-Cl-C₆H₄— | CH₃—(CH₂)₃—NH— | N | 114 |
| 80 | 4-Cl-C₆H₄— | CH₃—(CH₂)₂—NH— | N | 118 |
| 81 | 4-Cl-C₆H₄— | (CH₃)₂CH—CH₂—NH— | N | 140 |
| 82 | 4-Cl-C₆H₄— | C₆H₅—CH₂—NH— | N | 162 |
| 83 | 4-Cl-C₆H₄— | —NH—CH₂—C₆H₄-4-Cl | N | 138 |

TABLE 2-continued
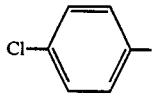
(I)
| Example No. | Ar | R | Z | Melting point [°C.] |
|---|---|---|---|---|
| 84 | 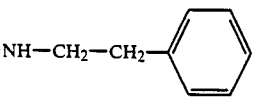 4-Cl-C6H4 | —NH—CH2—CH2—C6H5 | N | 108 |
| 85 | 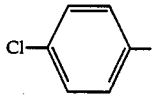 4-Cl-C6H4 | —NH—(CH2)5—CH3 | N | 84 |
| 86 |  4-Cl-C6H4 | —NH—CH2—cyclohexyl | N | 98 |
| 87 | 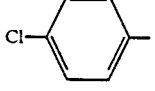 4-Cl-C6H4 | —NH—(CH2)11—CH3 | N | 88 |
| 88 | 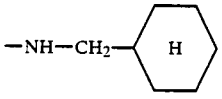 4-Cl-C6H4 | —NH—CH2—CH2—OCH3 | N | 106 |
| 89 | 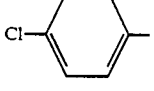 4-Cl-C6H4 | —NH—(CH2)3—OCH3 | N | 68 |
| 90 |  4-CH3-C6H4 | —CH2—(2,4-Cl2-C6H3) 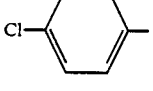 | N | 90 |
| 91 | 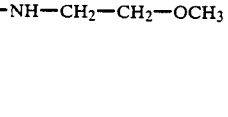 4-F-C6H4 | 3-F-C6H4 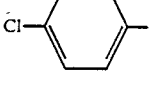 | N | 130 |
| 92 | 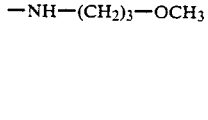 4-F-C6H4 | 2,6-F2-C6H3 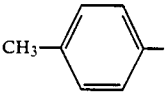 | N | 118 |
| 93 | 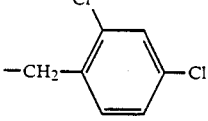 4-F-C6H4 | 4-CF3-C6H4 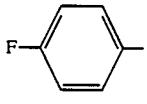 | N | 146 |

TABLE 2-continued

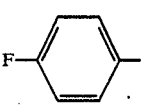

| Example No. | Ar | R | Z | Melting point [°C.] |
|---|---|---|---|---|
| 94 | F—⟨phenyl⟩— | 3-Br, 4-F-phenyl | N | 126 |
| 95 | F—⟨phenyl⟩— | 2-F, 4-Cl-phenyl | N | 144 |
| 96 | Cl—⟨phenyl⟩— | —CH(CH$_3$)$_2$ | N | 140 |
| 97 | Cl—⟨phenyl⟩— | —C(CH$_3$)$_3$ | N | 132 |
| 98 | F—⟨phenyl⟩— | 2-Br, 4-(1,2,4-triazolyl)-phenyl | N | 134 |
| 99 | Cl—⟨phenyl⟩— | —(CH$_2$)$_3$—CH$_3$ | N | n$_D^{20}$ = 1,5739 (refractive index) |
| 100 | F—⟨phenyl⟩— | 2-F, 3-Cl-phenyl | N | n$_D^{20}$ = 1.5933 (refractive index) |
| 101 | F—⟨phenyl⟩— | 2-Cl-phenyl | N | 102 |

USE EXAMPLES

In the following use examples, the compounds listed below were employed as comparison substances:

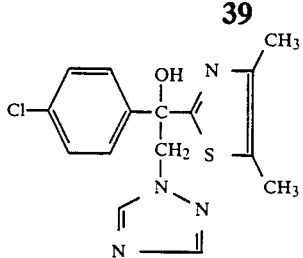

(A)

1-(4-chlorophenyl)-1-(4,5-dimethylthiazol-2-yl)-2-(1,2,4-triazol-1-yl)-ethanol

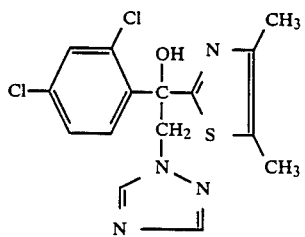

(B)

1-(2,4-dichlorophenyl)-1-(4,5-dimethylthiazol-2-yl)-2-(1,2,4-triazol-1-yl)-ethanol (both known from DE-OS (German Published Specification) 3,413,173)

EXAMPLE A

Leptosphaeria nodorum test (wheat)/protective

| Solvent: | 100 parts by weight of dimethylformamide |
|---|---|
| Emulsifier: | 0.25 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Leptosphaeria nodorum. The plants remain for 48 hours in an incubation cabin at 20° C. and 100% relative atmospheric humidity.

The plants are placed in a greenhouse at a temperature of about 15° C. and a relative atmospheric humidity of about 80%.

Evaluation is effected 10 days after the inoculation.

In this test, a substantially superior activity compared with the comparison substance (A) is shown by the compounds according to the invention and listed in Examples 1, 6, 7, 9, 10, 15, 17, 23, 28, 31, 32, 36, 37, 59, 60, 61, 62 and 68.

EXAMPLE B

Uromyces test (dwarf bean)/protective

| Solvent: | 4.7 parts by weight of acetone |
|---|---|
| Emulsifier: | 0.3 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous uredospore suspension of the bean rust causative organism (Uromyces appendiculatus) and remain in a dark humidity chamber at 20° to 22° C. and 100% relative atmospheric humidity for 1 day.

The plants are then placed in a greenhouse under intensive illumination at 20° to 22° C. and a relative atmospheric humidity of 70 to 80% for 9 days.

Evaluation is carried out 10 days after the inoculation.

In this test, a substantially superior activity compared with comparison substance (B) is shown by the active compounds according to the invention and listed in Examples 23, 25, 27, 28 and 40.

EXAMPLE C

Growth of cotton

| Solvent: | 30 parts by weight of dimethylformamide |
|---|---|
| Emulsifier: | 1 part by weight of polyoxyethylene sorbitan-monolaurate |

To produce a suitable preparation of active compound, 1 part by weight of active compound is mixed with the stated amounts of solvent and emulsifier, and the mixture is made up with water to the desired concentration.

Cotton plants are grown in the greenhouse until the fifth secondary leaf has completely unfolded. At this stage, the plants are sprayed with the preparations of the active compound until dripping wet. After two weeks, additional growth is measured on all plants, and growth is calculated in per cent of the additional growth of the control plants. 100% growth denotes growth corresponding to that of the control plants, and 0% denotes cessation of growth. Values greater than 100% denote increased growth.

In this test, the compound according to the invention mentioned in Example 28 shows a very strong growth-inhibiting action.

EXAMPLE D

Growth of soy beans

| Solvent: | 30 parts by weight of dimethylformamide |
|---|---|
| Emulsifier: | 1 part by weight of polyoxyethylene sorbitan monolaurate |

To produce a suitable preparation of active compound, 1 part by weight of active compound is mixed with the stated amounts of solvent and emulsifier, and the mixture is made up with water to the desired concentration.

Soy bean plants are grown in the greenhouse until the first secondary leaf has completely unfolded. At this stage, the plants are sprayed with the preparations of the active compound until dripping wet. After two weeks, the additional growth is measured on all plants, and growth is calculated in per cent of the additional growth of the control plants. 100% of growth denotes growth corresponding to that of the control plants, and 0% denotes the cessation of growth. Values greater than 100% denote an increase in growth.

In this test, the compound according to the invention mentioned in Example 16 shows a very strong growth-inhibiting action.

It will be understood that the specification and examples are illustrative, but not limitative of the present invention and that other embodiments within the spirit and scope of the invention will suggest themselves to those skilled in the art.

What is claimed is:

1. A substituted azolylmethylcarbinol of the formula

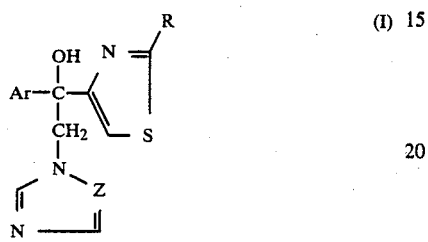

wherein

Ar stands for phenyl which can be monosubstituted or polysubstituted by identical or different substituents from the series comprising halogen, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different halogen atoms, straight-chain or branched halogenoalkoxy having 1 to 4 carbon atoms and 1 to 9 identical or different halogen atoms, and/or by straight-chain or branched halogenoalkylthio having 1 to 4 carbon atoms and 1 to 9 identical or different halogen atoms, Z stands for nitrogen or a CH group, and R stands for straight-chain or branched alkyl having 1 to 6 carbon atoms, straight-chain or branced dialkylaminoalkyl having 1 to 4 carbon atoms in each alkyl group, straight-chain or branched alkenyl having 3 to 6 carbon atoms, straight-chain or branched alkinyl having 3 to 6 carbon atoms, straight-chain or branched alkoxyalkyl having 1 to 6 carbon atoms in the alkyl moiety and 1 to 6 carbon atoms in the alkoxy moiety, or R stands for aralkyl having 1 to 4 carbon atoms in the alkyl moiety and 6 to 10 carbon atoms in the aryl moiety, where the aryl moiety can be monosubstituted or polysubstituted by identical or different substituents from the series comprising halogen, cyano, nitro, phenyl, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different halogen atoms, straight-chain or branched halogenoalkoxy having 1 to 4 carbon atoms, and 1 to 9 identical or different halogen atoms, and/or by straight-chain or branched halogenoalkylthio having 1 to 4 carbon atoms and 1 to 9 identical or different halogen atoms, or by a five- or six-membered nitrogen containing heterocyclic ring, linked via N, which can optionally contain further heteroatoms and which can be monosubstituted or polysubstituted by identical or different substituents from the series comprising straight-chain or branched alkyl having 1 to 4 carbon atoms, straight-chain or branched alkoxycarbonyl having 1 to 4 carbon atoms in the alkoxy moiety and/or by alkylcarbamoyl having 1 to 4 carbon atoms in the alkyl moiety, or R stands for aryloxyalkyl having 1 to 4 carbon atoms in the alkyl moiety and 6 to 10 carbon atoms in the aryl moiety, where the aryl moiety can be monosubstituted or polysubstituted by identical or different substituents from the series comprising halogen, cyano, nitro, phenyl, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different halogen atoms, straight-chain or branched halogenoalkoxy having 1 to 4 carbon atoms and 1 to 9 identical or different halogen atoms, and/or by straight-chain or branched halogenoalkylthio having 1 to 4 carbon atoms and 1 to 9 identical or different halogen atoms, or by a five- or six-membered nitrogen containing heterocyclic ring, linked via N, which can optionally contain further heteroatoms and which can be monosubstituted or polysubstituted by identical or different substituents from the series comprising straight-chain or branched alkyl having 1 to 4 carbon atoms, straight-chain or branched alkoxycarbonyl having 1 to 4 carbon atoms in the alkoxy moiety and/or by alkylcarbamoyl having 1 to 4 carbon atoms in the alkyl moiety, or R stands for aryl having 6 to 10 carbon atoms, where the aryl radical can be monosubstituted or polysubstituted by identical or different substituents from the series comprising halogen, cyano, nitro, phenyl, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different halogen atoms, straight-chain or branched halogenoalkoxy having 1 to 4 carbon atoms and 1 to 9 identical or different halogen atoms and/or by straight-chain or branched halogenoalkylthio having 1 to 4 carbon atoms and 1 to 9 identical or different halogen atoms, by a five- or six-membered nitrogen containing heterocyclic ring, linked via N, which can optionally contain further heteroatoms and which can be monosubstituted or polysubstituted by identical or different substituents from the series comprising straight-chain or branched alkyl having 1 to 4 carbon atoms, straight-chain or branched alkoxycarbonyl having 1 to 4 carbon atoms in the alkoxy moiety and/or by alkylcarbamoyl having 1 to 4 carbon atoms in the alkyl moiety, or R stands for a radical of the formula

wherein

R[1] stands for hydrogen, straight-chain or branched alkyl having 1 to 6 carbon atoms, straight-chain or branched alkenyl having 2 to 6 carbon atoms, straight-chain or branched alkinyl having 2 to 6 carbon atoms or for cycloalkyl having 3 to 7 carbon atoms, and R[2] stands for hydrogen, straight-chain or branched alkyl having 1 to 16 carbon atoms, straight-chain or branched alkoxyalkyl having 1 to 4 carbon atoms in the alkyl part and 1 to 4 carbon atoms in the alkoxy part, straight-chain or branched alkenyl having 2 to 6 carbon atoms, straight-chain or branched alkinyl having 2 to 6 carbon atoms, cycloalkyl having 3 to 7 carbon atoms, cycloalkylalkyl having 3 to 7 carbon atoms in the cycloalkyl part and 1 to 4 carbon atoms in the alkyl part, or for phenyl which can be monosubstituted or polysubstituted by identical or different substituents from the series comprising halogen, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different halogen atoms, straight-chain or branched halogenoalkoxy having 1 to 4 carbon atoms and 1 to 9 identical or different halogen atoms and/or by straight-chain or branched halogenoalkylthio having 1 to 4 carbon atoms and 1 to 9 identical or different halogen atoms, or R[2] stands for aralkyl having 1 to 4 carbon atoms in the alkyl moiety and 6 to 10 carbon atoms in the aryl moiety, wherein the aryl moiety can be monosubstituted or polysubstituted by identical or different substituents from the series comprising halogen, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different halogen atoms, by straight-chain or branched halogenoalkoxy having 1 to 4 carbon atoms and 1 to 9 identical or different halogen atoms, and/or by straight-chain or branched halogenoalkylthio having 1 to 4 carbon atoms and 1 to 9 identical or different halogen atoms, or R[1] and R[2] together with the nitrogen atom to which they are bonded stand for a saturated 5- to 7-membered heterocyclic ring, where the heterocyclic ring can contain a further heteroatom, and where the heterocyclic ring can be monosubstituted or polysubstituted by identical or different substituents from the series comprising straight-chain or branched alkyl having 1 to 4 carbon atoms, straight-chain or branched hydroxyalkyl having 1 to 4 carbon atoms, straight-chain or branched alkanoyl having 1 to 4 carbon atoms in the alkane moiety and/or by alkanoyloxyalkyl having 1 to 4 carbon atoms in the alkane moiety and 1 to 4 carbon atoms in the oxyalkyl moiety, or an addition product thereof with acid or metal salt.

2. A compound as claimed in claim 2, wherein

Ar stands for phenyl which can be monosubstituted, disubstituted or trisubstituted by identical or different substituents from the series comprising fluorine, chlorine, bromine, methyl, ethyl, n- or i-propyl, n-, i-, s- or t-butyl, methoxy, ethoxy, n- or i-propoxy, methylthio, trifluoromethyl, trifluoromethoxy or trifluoromethylthio, Z stands for nitrogen or a CH group and R stands for methyl, ethyl, n- or i-propyl, n-, i-, s- or t-butyl, dimethylaminopropyl, allyl, n- or i-butenyl, propargyl, methoxymethyl, methoxyethyl, ethoxymethyl, ethoxyethyl, n- or i-propoxymethyl, n- or i-propoxyethyl, or for benzyl, phenylethyl, phenoxymethyl or phenyl, where each of these benzyl, phenylethyl, phenoxymethyl or phenyl radicals can be monosubstituted, disubstituted or trisubstituted by identical or different substituents from the series comprising fluorine, chlorine, bromine, methyl, ethyl, n- or i-propyl, n-, i-, s- or t-butyl, methoxy, ethoxy, n- or i-propoxy, methylthio, trifluoromethyl, trifluoromethoxy, trifluoromethylthio, phenyl, triazolyl which is optionally monosubstituted, disubstituted or trisubstituted by identical or different substituents from the series comprising methyl, ethyl, methoxycarbonyl, ethoxycarbonyl, methylcarbamoyl or ethylcarbamoyl, imidazolyl which is optionally monosubstituted, disubstituted or trisubstituted by identical or different substituents from the series comprising methyl, ethyl, methoxycarbonyl, ethoxycarbonyl, methylcarbamoyl or ethylcarbamoyl, pyrazolyl which is optionally monosubstituted, disubstituted or trisubstituted by identical or different substituents from the series comprising methyl, ethyl, methoxycarbonyl, ethoxycarbonyl, methylcarbamoyl or ethylcarbamoyl, pyrrolidinyl which is optionally monosubstituted, disubstituted or trisubstituted by identical or different substituents from the series comprising methyl, ethyl, methoxycarbonyl, ethoxycarbonyl, methylcarbamoyl or ethylcarbamoyl, piperidinyl which is optionally monosubstituted, disubstituted or trisubstituted by identical or different substituents from the series comprising methyl, ethyl, methoxycarbonyl, ethoxycarbonyl, methylcarbamoyl or ethylcarbamoyl, morpholinyl which is optionally monosubstituted, disubstituted or trisubstituted by identical or different substituents from the series comprising methyl, ethyl, methoxycarbonyl, ethoxycarbonyl, methylcarbamoyl or ethylcarbamoyl, and/or piperazinyl which is optionally monosubstituted, disubstituted or trisubstituted by identical or different substituents from the series comprising methyl, ethyl, methoxycarbonyl, ethoxycarbonyl, methylcarbamoyl or ethylcarbamoyl, or R stands for a radical of the formula

wherein

R¹ stands for hydrogen, methyl, ethyl, n- or i-propyl, n-, i-, s- or t-butyl, allyl, n- or i-butenyl, propargyl, n- or i-butinyl, cyclopentyl or cyclohexyl and R² stands for hydrogen, methyl, ethyl, n- or i-propyl, n-, i-, s- or t-butyl, hexyl or n-dodecyl, methoxymethyl, methoxyethyl, ethoxymethyl, ethoxyethyl, methoxypropyl, ethoxypropyl, allyl, n- or i-butenyl, propargyl, n-or i-butinyl, cyclopentyl, cyclohexyl, cyclopentylmethyl, cyclohexylmethyl, or for phenyl which can be monosubstituted, disubstituted or trisubstituted by identical or different substituents from the series comprising fluorine, chlorine, bromine, methyl, ethyl, n- or i-propyl, n-, i-, s- or t-butyl, methoxy, ethoxy, n- or i-propoxy, methylthio, trifluoromethyl, trifluoromethoxy and/or trifluoromethylthio, or R² stands for benzyl or phenethyl, wherein each of these radicals can be monosubstituted, disubstituted or trisubstituted in the phenyl part by identical or different substituents from the series comprising fluorine, chlorine, bromine, methyl, ethyl, n- or i-propyl, n-, i-, s- or t-butyl, methoxy, ethoxy, n- or i-propoxy, methylthio, trifluoromethyl, trifluoromethoxy and/or trifluoromethylthio, or R¹ and R² together with the nitrogen atom to which they are bonded stand for pyrrolidinyl, piperidinyl, hexahydroazepinyl, morpholinyl, thiamorpholinyl or 1,4-piperazinyl, where each of the mentioned radicals can be monosubstituted, disubstituted or trisubstituted by identical or different substituents from the series comprising methyl, ethyl, hydroxymethyl, acetyl, propionyl and/or acetoxymethyl, or an addition product thereof with an acid or a metal salt.

3. A compound as claimed in claim 2, wherein such compound is a substituted azolylmethylcarbinol of the formula

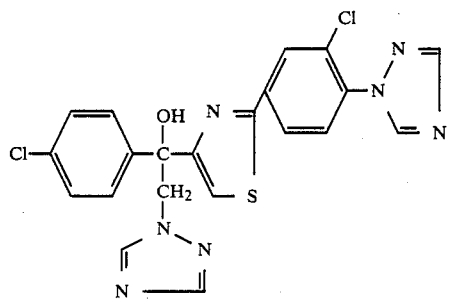

4. A compound as claimed in claim 2, wherein such compound is a substituted azolylmethylcarbinol of the formula

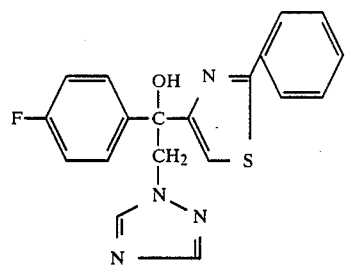

5. A compound as claimed in claim 2, wherein such compound is a substituted azolylmethylcarbinol of the formula

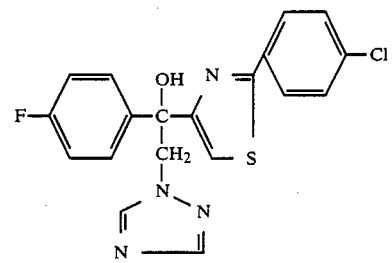

6. A compound as claimed in claim 2, wherein such compound is a substituted azolylmethylcarbinol of the formula

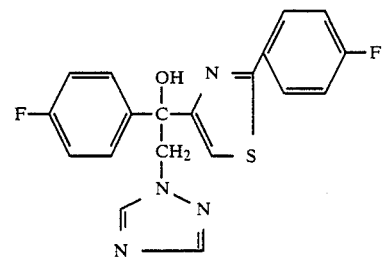

7. A compound as claimed in claim 2, wherein such compound is a substituted azolylmethylcarbinol of the formula

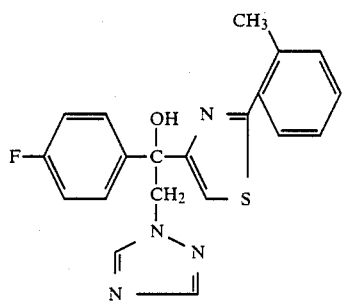

8. A compound as claimed in claim 2, wherein such compound is a substituted azolylmethylcarbinol of the formula

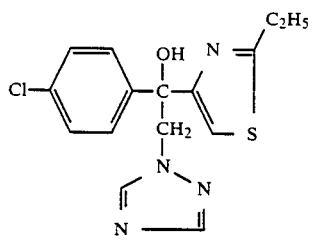

9. A fungicidal composition comprising a fungicidally effective amount of a compound or addition product according to claim 2 in admixture with a diluent.

10. A method of combating fungi which comprises administering to such fungi or to a fungus habitat a fungicidally effective amount of a compound or addition product according to claim 2.

11. The method according to claim 10, wherein such compound is a substituted azolylmethylcarbinol of the formula selected from

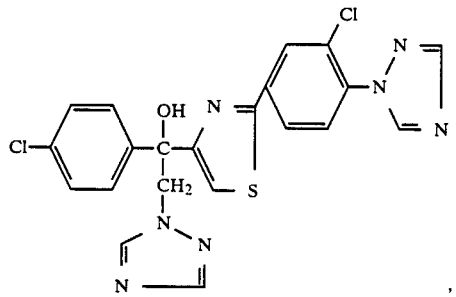

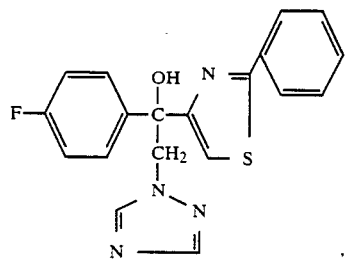

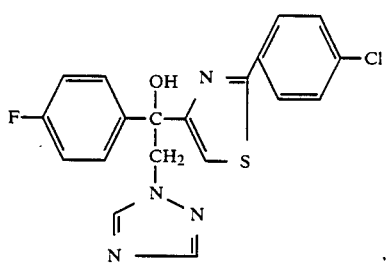

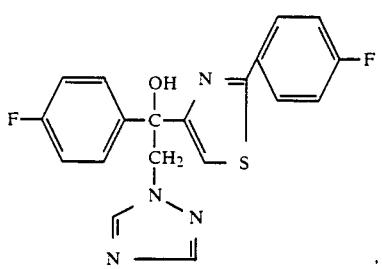

-continued

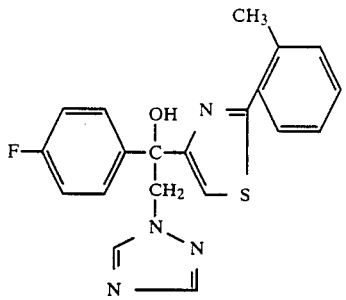

and

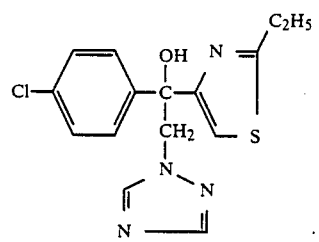

12. A plant growth regulating composition comprising a plant growth regulatingly effective amount of a compound or addition product according to claim 2 in admixture with a diluent.

13. A method of regulating plant growth which comprises administering to the plants or to their habitat a plant growth regulatingly effective amount of a compound or addition product according to claim 2.

14. The method according to claim 13, wherein such compound is a substituted azolylmethylcarbinol of the formula selected from

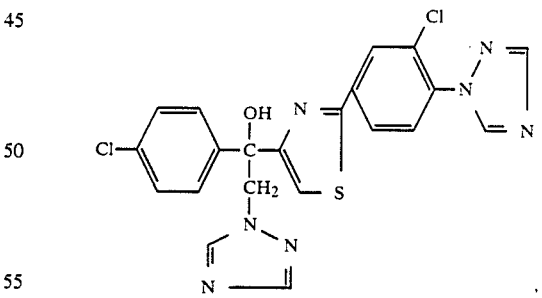

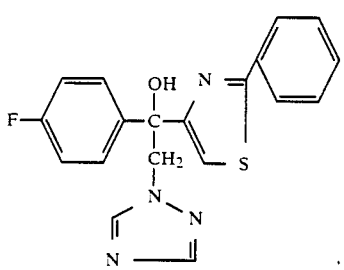

-continued
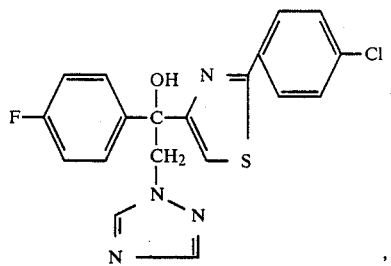
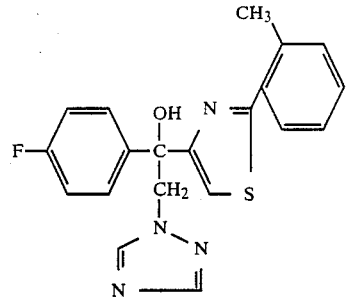
and
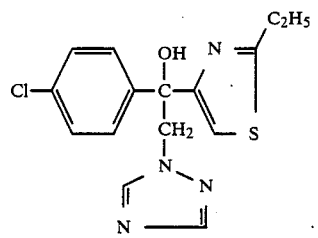
* * * * *

UNITED STATES PATENT AND TRADEMARK OFFICE
CERTIFICATE OF CORRECTION

PATENT NO. : 4,935,049

DATED : June 19, 1990

INVENTOR(S) : Kramer et al.

It is certified that error appears in the above-identified patent and that said Letters Patent is hereby corrected as shown below:

| | |
|---|---|
| Title Page | Add -- U.S. PATENT DOCUMENTS: 4,657,920, 4/1987, Gajowski et al., 548/205 -- |
| Title Page | ABSTRACT : 5 lines from bottom delete " cna " and substitute -- can -- |
| Col. 44, claim 2 line 5 | After " claim " delete " 2 " and substitute -- 1 -- |
| Col. 45, claims 3-4 lines 47 & 65 | After " claim " delete " 2 " and substitute -- 1 -- |
| Col. 46, claims 5-8 lines 14, 31, 48 & 66 | After " claim " delete " 2 " and substitute -- 1 -- |
| Col. 47, claims 9-10 lines 14 & 18 | After " claim " delete " 2 " and substitute -- 1 -- |
| Col. 48, claims 12-13 lines 31 & 37 | After " claim " delete " 2 " and substitute -- 1 -- |

UNITED STATES PATENT AND TRADEMARK OFFICE
CERTIFICATE OF CORRECTION

PATENT NO. : 4,935,049

DATED : June 19, 1990

INVENTOR(S) : Kramer et al.

It is certified that error appears in the above-identified patent and that said Letters Patent is hereby corrected as shown below:

Col. 48, claims 12-13 lines 31 & 37    After " claim " delete " 2 " and substitute -- 1 --

Signed and Sealed this

Eighteenth Day of February, 1992

Attest:

HARRY F. MANBECK, JR.

*Attesting Officer*    Commissioner of Patents and Trademarks